United States Patent [19]
Zichner et al.

[11] Patent Number: 5,425,778
[45] Date of Patent: Jun. 20, 1995

[54] ACETABULAR SOCKET SUPPORTING RING

[75] Inventors: Ludwig Zichner, Neu-Isenburg, Germany; Thomas Wahl, Lengnau; Beat Leu, Hergiswil, both of Switzerland

[73] Assignee: Oscobal AG, Selzach, Switzerland

[21] Appl. No.: 132,948

[22] Filed: Oct. 7, 1993

[30] Foreign Application Priority Data

Oct. 7, 1992 [EP] European Pat. Off. ........... 92810761

[51] Int. Cl.6 .............................................. A61F 2/34
[52] U.S. Cl. ......................................... 623/22; 623/18
[58] Field of Search ...................... 623/16, 18, 19, 22, 623/23

[56] References Cited

U.S. PATENT DOCUMENTS

| | | |
|---|---|---|
| 3,863,273 | 2/1975 | Averill . |
| 4,623,351 | 11/1986 | Church . |
| 4,770,658 | 9/1988 | Geremakis ........................... 623/22 |
| 4,919,674 | 4/1990 | Schelhas ............................. 623/22 |

FOREIGN PATENT DOCUMENTS

| | | | |
|---|---|---|---|
| 0123514 | 10/1984 | European Pat. Off. ............. 623/22 |
| 0285756 | 10/1988 | European Pat. Off. ............. 623/22 |
| 0313773 | 5/1989 | European Pat. Off. . |
| 0486403 | 5/1992 | European Pat. Off. . |
| 0501207 | 9/1992 | European Pat. Off. ............. 623/22 |
| 2233976 | 1/1975 | France . |
| 2287209 | 10/1975 | France ............................... 623/22 |
| 2634372 | 1/1990 | France ............................... 623/22 |
| 2660546 | 10/1991 | France ............................... 623/22 |
| 4102510 | 7/1992 | Germany . |

*Primary Examiner*—David Isabella
*Attorney, Agent, or Firm*—Marks & Murase

[57] ABSTRACT

The actabular socket supporting ring has a modular construction and is formed of a supporting ring having two securing straps for a cement-free attachment in and on the corresponding bone portions, of a socket cup which is pivotably adjustable in the supporting ring and attachable to the supporting ring by a securing element without the use of bone cement, and of an insert receiving the joint head. The modular construction, and in particular, the pivotable arrangement of the socket cup in the supporting ring, allows a biomechanically optimal alignment of the socket cup, and thus, of the insert receiving the joint ball, and the securing of the socket cup to the supporting ring by a securing element allows an entirely cement-free anchorage of all components.

10 Claims, 3 Drawing Sheets

ACETABULAR SOCKET SUPPORTING RING

BACKGROUND OF THE INVENTION

The present invention refers to an acetabular socket supporting ring comprising a supporting ring having at least one attaching strap for a cement-free attachment in and on the corresponding bone portions, a socket cup comprising a part for receiving the joint ball, the socket cup being pivotably adjustable in the supporting ring and capable of being attached to the supporting ring by a securing element without the use of bone cement. Such an acetabular socket is known from the European Patent Application No. 0 123 514. Whilst therein the idea of adjusting the socket cup is disclosed, the securing element is relatively complicated and limited.

Acetabular socket supporting rings are known in further different embodiments and are mainly used in problematic hip joint revision operations. In particular, such problems result from the bone-resorbing action of the bone cement, mostly causing large-volume bone defects. In this case, the anchorage of a standardized cement-free acetabular implant is generally extremely difficult. In the case of dysplastic hips, as well, an anchorage of the hip joint socket is very problematic.

The supporting implants of this prior art are secured in the acetabulum by bone screws, and the hip joint socket is cemented in by bone cement. However, such an arrangement again involves the known drawbacks of the use of bone cement, more particularly a bone-resorbing action and an insufficient long-term vibration resistance, whereby the implant is loosened. Besides the need of using bone cement for the anchorage of the socket, the previously known socket supporting rings have the further disadvantage of being insertable in the pelvis in the exactly correct position only to a limited extent.

Based on the above mentioned prior art, it is the object of the present invention to provide an acetabular socket supporting ring which allows a cement-free implantation, on one hand, and a more precise, secure and simpler alignment of the socket in the pelvis and thus also with respect to the shaft, on the other hand.

This object is attained by an acetabular socket supporting ring, comprising a supporting ring having at least one attaching strap for a cement-free attachment in and on the corresponding bone portions, a socket cup comprising a part for receiving the joint ball, the socket cup being pivotably adjustable in the supporting ring and capable of being attached to the supporting ring by a securing element without the use of bone cement, wherein the supporting ring is internally provided with a cylindrical portion having an internal thread for receiving the securing element which has a self-locking external thread, and with a following spherical portion for receiving the socket cup, and wherein the part for receiving the joint ball is an insert, generally of plastics material.

In the first place, no bone cement is used for the anchorage of the socket supporting ring, and furthermore, the modular design allows a very precise adjustment of the socket cup.

BRIEF DESCRIPTION OF THE DRAWINGS

The invention is described in more detail hereinafter with reference to a drawing of an embodiment.

DETAILED DESCRIPTION OF THE INVENTION

Figure 1:
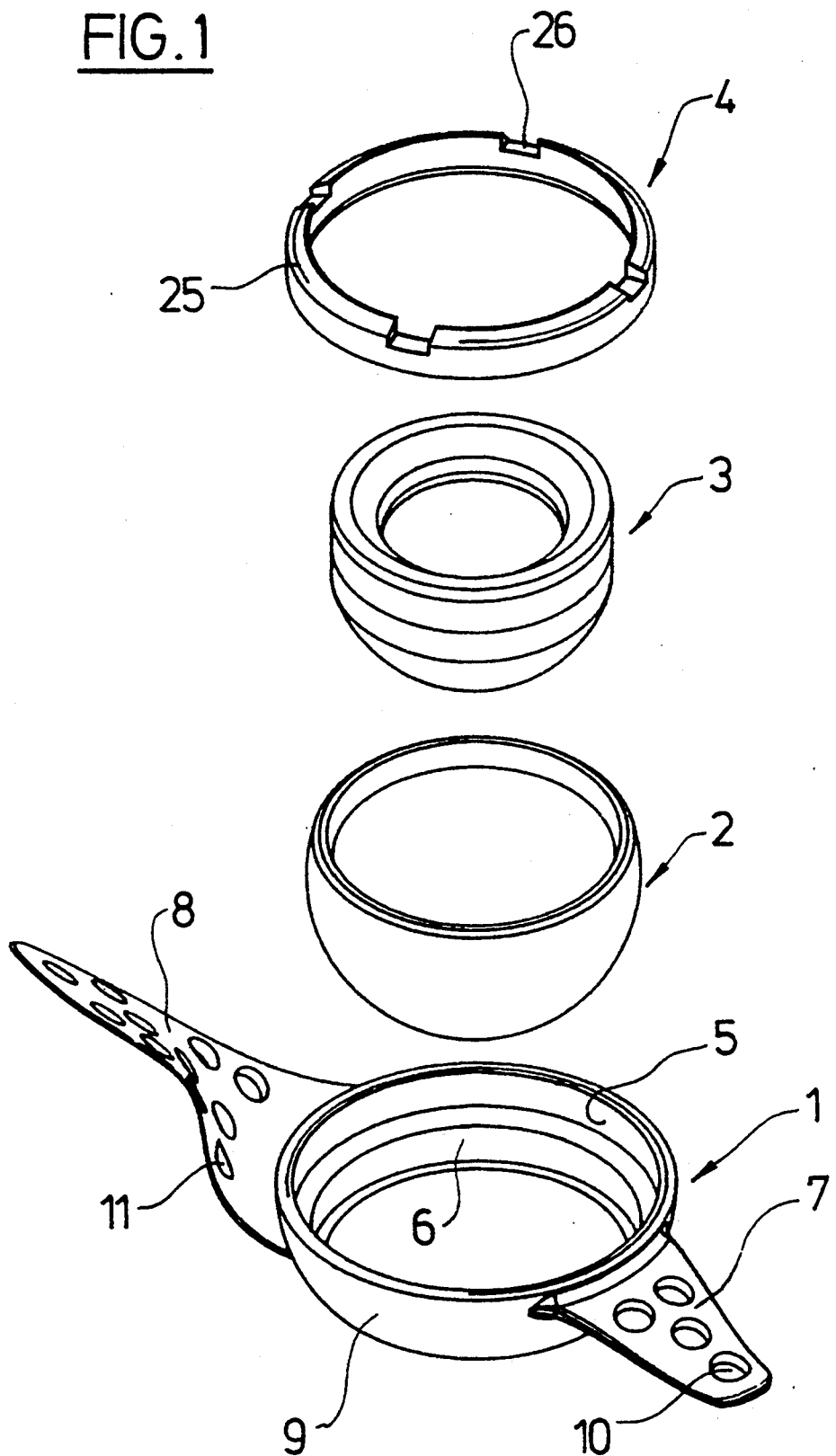
FIG. 1 shows a schematic exploded view of the four parts of the socket supporting ring of the invention.

FIG. 1 shows the four elements of the socket supporting ring, namely, from bottom to top, supporting ring 1, socket cup 2, insert 3, and a securing ring 4 which serves as a securing element, the insert being made of plastics material, preferably of polyethylene, or at least partially of metal, and the other parts being made of metal, e.g. titanium, a titanium alloy, or a chrome-cobalt-molybdenum alloy, or also of plastics material. As appears most clearly in FIGS. 1 and 3, the supporting ring comprises a cylindrical portion 5 with an internal thread for receiving said securing ring, followed by a spherical, concentrical portion 6 receiving socket cup 2. Externally, the supporting ring is provided with a small strap 7 and a large strap 8. The surfaces of all metal parts which are in contact with the bone, including surface 9 of the supporting ring, may be treated in order to improve the accretion of the bone. For example, the surface may be increased by glass-blasting or be provided with a hydroxyl apatite or a similarly bioactive coating, e.g., also a calcium phosphate glass, which may also be sputtered on. This ensures long-term stability by accretion or ingrowth of the bone to respectively grow into the implant.

Primary stability is obtained by the two straps 7 and 8. The smaller strap 7 is anatomically shaped, i.e., tapering to a point and provided with bores 10 in which the bone can grow in, thus resulting in an increased retaining stability. The smaller strap is generally driven into the pubis. If this is not possible, i.e., if the anchorage of the ring is prohibited by an insufficient solidity of the bone in the pubic area, the supporting ring may be secured by screws passing through the holes 10. The configuration of the screw holes not only allows to implant said the screws in the axis of the bores but also to tilt them to a certain extent. The edges of the smaller strap 7 are shaped in such a manner that a penetration of the strap is possible without bursting the bone. Since the entire small strap is anchored in the bone, it is preferred to treat its entire surface.

Figure 2:
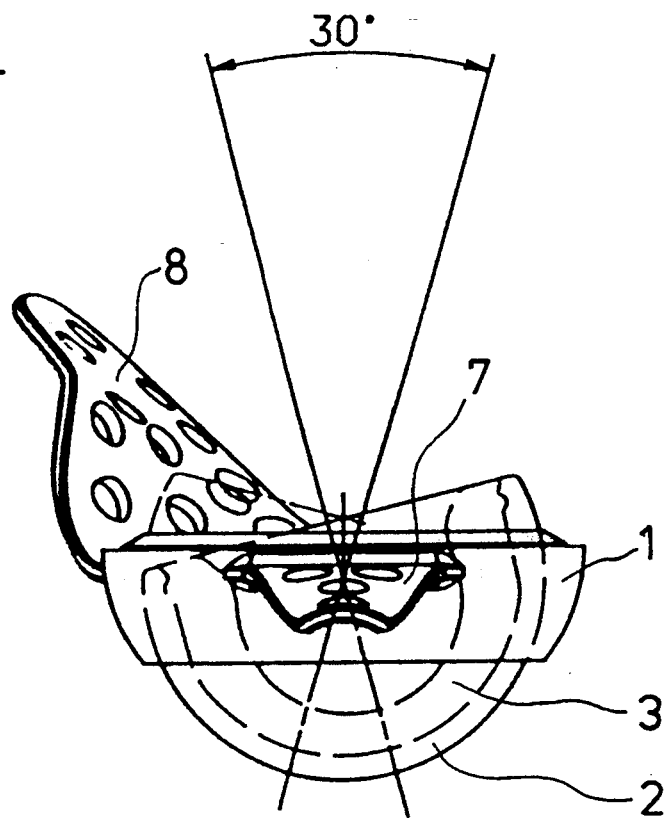
FIG. 2 shows a side elevation of the assembled socket supporting ring of FIG. 1.
Figure 3:
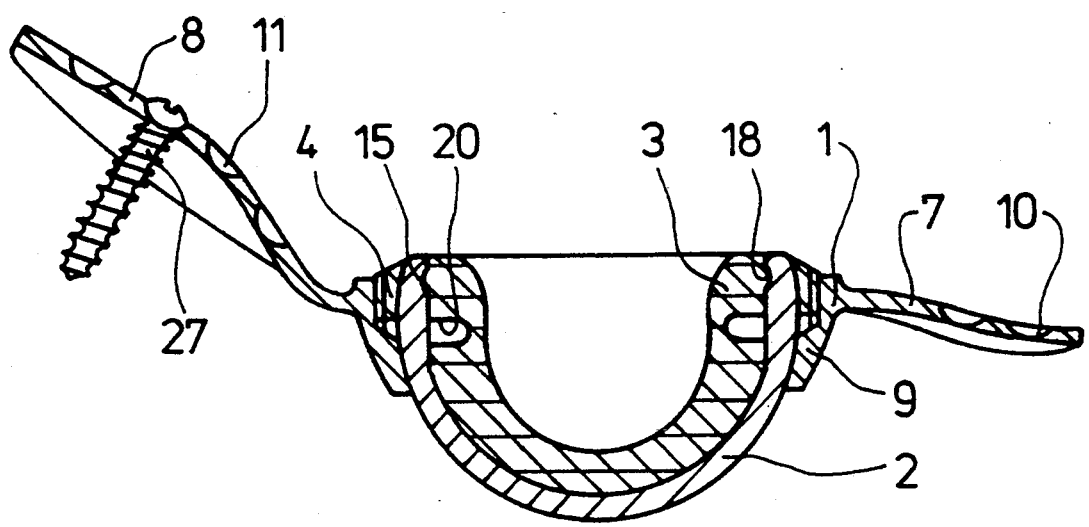
FIG. 3 is a sectional view of the illustration of FIG. 2.

Anatomically shaped larger strap 8 is arranged opposite small strap 7 and axially displaced by 15° to 30°, as is best visible in FIGS. 2 and 3. It is understood that the two straps are adapted to the anatomical conditions. In contrast to the smaller strap, the longer one is not driven in but is placed on the pelvis bone and secured there by bone screws 27 which may be spongiosa or cortical screws. Depending on intraoperative conditions, the longer strap may possibly be adapted to the anatomical conditions. On one hand, the longer strap serves to ensure a sufficient primary stability of the implant, and on the other hand, for a long-term physiological force transmission of the existing stresses to the acetabulum. Here also, the screws are allowed to tilt in bores 11 within a certain range since the bores are spherically countersunk.

Figure 5:
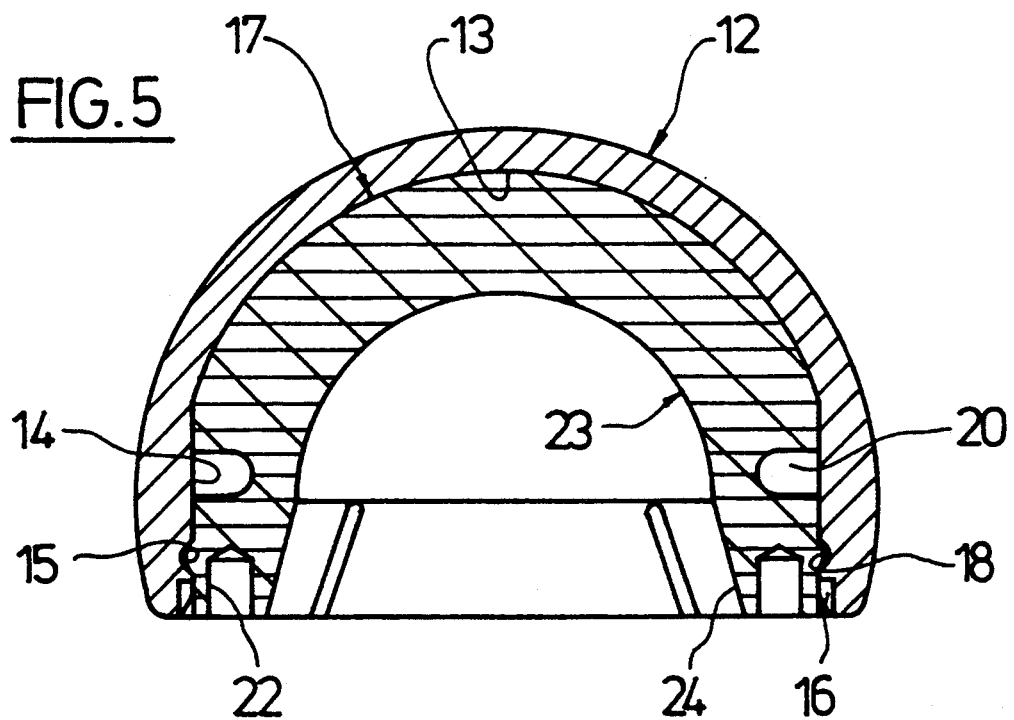
FIG. 5 shows a sectional view of the insert when inserted in the socket cup.

Socket cup 2 is externally provided with a spherical surface 12 (see especially FIG. 5) which is best adapted to the anatomical conditions and which provides an even and thus physiological force transmission on a large surface. Also the external surface of the socket cup which is beyond the enclosed area may be provided with means favoring an accretion of the bone. Thus, the external surface may have a surface-increasing spherular coating or a coating of a bioactive material such as hydroxil apatite or the like, or it may be roughened.

Internal surface 13 of the socket cup is also largely spherical, but near the external rim it has a cylindrical surface 14 in which a circular groove 15 and, close to the edge, recesses 16 are arranged. Circular groove 15 as well as recesses 16 serve for securing insert 3, as will be explained in more detail herebelow. The cylindrical portion of the socket cup takes up the friction moment which is transmitted from the hip joint ball to the insert and thus prevents a dislocation of the insert.

Insert 3 is preferably made of polyethylene and is intended to receive the hip joint ball. External surface 17 of the insert corresponds to internal surface 13 and 14 of the socket cup, a bead 18 corresponding to groove 15. Bead 18 does not extend over the entire circumference here, but it is only arranged sectorwise. For rotational securing, the insert is provided with projections 19 corresponding to recesses 16, the number of recesses and projections, respectively, being chosen at will.

Figure 4:
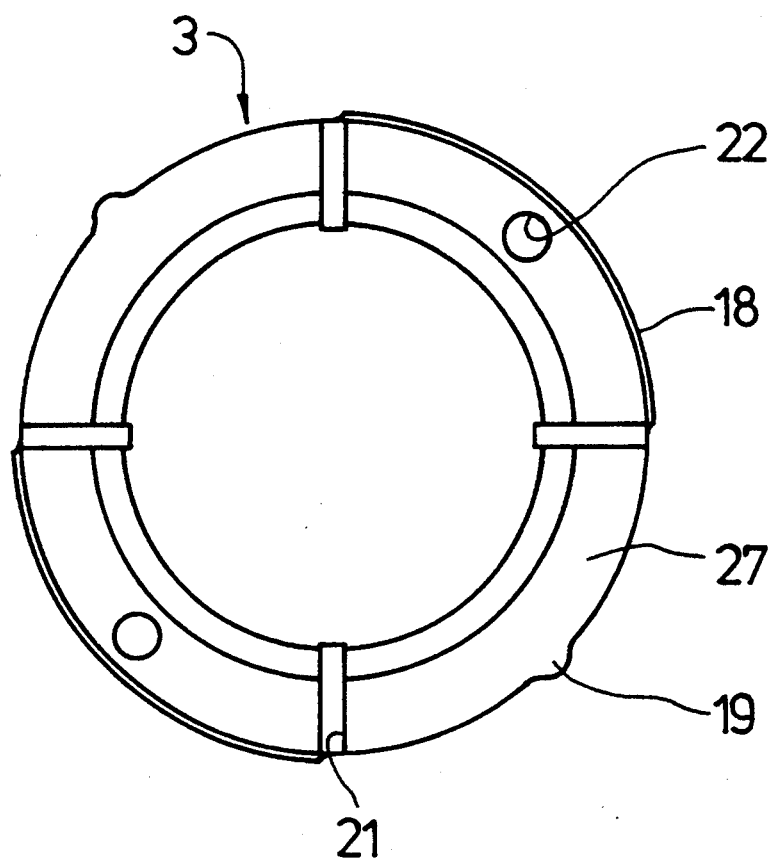
FIG. 4 shows the insert as seen from the bottom.

Since it may occur that the insert must be exchanged, several measures have to be taken in this respect. It is thus useful that the bead does not extend over the entire circumference but only over, e.g., two times 90°, as suggested in FIG. 4. Moreover, the bead must be lifted out of the groove if the insert is supposed to be removed, which is only possible if the insert is compressible. This is possible by providing an incision 20 approximately in the inner third of the cylindrical portion, and by, e.g., four grooves in annular surface 25 of the insert. By these measures, a certain flexibility of the cylindrical portion of the insert is obtained, and it is thus possible, by an instrument engaging in two bores 22 which are arranged near beads 18, to compress the cylindrical portion of said insert.

Internal surface 23 of the insert is in the known shape of the hip joint socket, comprising a spherical surface which is followed by an enlarged portion 24 in order to allow an increased freedom of motion. A mechanical clamping of the joint head for luxation prevention is possible in the case where internal surface 23 projects over the equator.

Securing ring 4 comprises a self-locking external thread 25 corresponding to the internal thread of internal cylindrical portion 5 of the supporting ring. The internal diameter of said securing ring is slightly larger than the external diameter of the socket cup, resulting in a good clamping action of the securing ring. In order to allow the securing ring to be screwed in and locked, its front side is provided with grooves 26 or bores or the like.

Instead of the previously described clamping ring, other clamping devices may be used as well in order to secure the socket cup in the aligned position.

After anchoring the supporting ring in the corresponding bone portions, the socket cup is inserted and aliged in order to bring it to the biomechanically optimal position, as indicated in FIG. 2, a tilting range of 30° being assumed which is normally sufficient. Subsequently, the socket cup is immovably secured by securing ring 4. Polyethylene insert 3 can then be inserted in the socket cup and snapped in. By the possibility of tilting the socket cup in a wide range of angles and thus positioning it in an optimal manner, and by the cement-free securing of the socket cup in the supporting ring, a very high long-term stability and a maximum freedom of motion is obtained.

We claim:

1. An acetabular socket system, comprising:
    a supporting ring having at least one attaching strap extending outwardly therefrom for a cement-free attachment in and on the corresponding bone portions;
    a socket cup comprising a cavity configured for receiving a bearing insert, said bearing insert including a spherical cavity for receiving a joint ball element, said socket cup being pivotably adjustable in said supporting ring and having attachment means for attaching the supporting ring to the socket cup without the use of bone cement;
    said supporting ring being internally provided with a cylindrical portion having an internal thread for receiving said securing element which has a self-locking external thread, and with a following spherical portion for receiving said socket cup.

2. The socket system of claim 1, wherein said supporting ring comprises two attachment straps having holes formed therein for attachment to the bone portions with one of said attachment straps being shorter than the other.

3. The socket systems of claim 1, wherein said socket cup has a spherical external surface and an internal surface formed of a cylindrical portion and a spherical portion, said cylindrical portion comprising means for securing said insert, and said insert having an external surface which corresponds to the internal surface of said socket cup and is provided with corresponding securing means.

4. The socket system of claim 1, wherein said insert is made of a material selected from the group consisting of polyethylene and metal and combinations thereof, and wherein said insert comprises means for removing said insert from said socket cup.

5. The socket system of claim 3, wherein said means for securing said insert in said socket cup comprises a circular groove and recesses formed in said socket cup, and beads and projections formed on said insert.

6. The socket system of claim 1, wherein said insert is removable, said cylindrical portion having an external incision, and said annular surface having grooves and bores at locations where a bead is arranged, in order to allow said insert to be compressed near a front surface of said insert and to be removed from said socket cup by a tool engaging in said bores.

7. The socket system of claim 1, wherein the portions of said supporting ring and of said socket cup which are in contact with the bone are provided with bioactive means.

8. The socket system of claim 7, wherein said bioactive means comprises a coating of a material selected from the group consisting of hydroxyl apatite, calcium phosphate, and glass.

9. The socket system of claim 1, wherein said supporting ring, said socket cup and said securing ring are made of a material selected from the group consisting of a chromium-cobalt-molybdenum alloy, titanium, a titanium alloy, and plastic.

10. The socket system of claim 7, wherein said bioactive means comprises a coating having a roughened external surface.

* * * * *